United States Patent [19]

Joyce et al.

[11] 4,415,585

[45] Nov. 15, 1983

[54] CONTRACEPTIVE METHOD

[75] Inventors: Cathy L. Joyce, Oak Park; Lourens J. D. Zaneveld, Chicago, both of Ill.

[73] Assignee: University of Illinois Foundation, Urbana, Ill.

[21] Appl. No.: 357,160

[22] Filed: Mar. 11, 1982

[51] Int. Cl.³ .................... A61K 31/53; A61K 31/415
[52] U.S. Cl. .............................. 424/273 P; 424/249; 424/DIG. 14
[58] Field of Search .................. 424/273 P, DIG. 14, 424/249

[56] References Cited

U.S. PATENT DOCUMENTS

| | | | |
|---|---|---|---|
| 3,752,894 | 8/1973 | Esteve | 424/273 P |
| 3,760,080 | 9/1973 | Urwyler | 424/273 P |
| 3,833,729 | 9/1974 | Negrevergne | 424/273 P |
| 4,216,212 | 8/1980 | Flora et al. | 424/273 P |
| 4,255,438 | 3/1981 | Kane et al. | 424/273 P |

*Primary Examiner*—Leonard Schenkman
*Attorney, Agent, or Firm*—Merriam, Marshall & Bicknell

[57] ABSTRACT

Contraceptive method comprises maintaining in the genital tract of a female mammal a pyrazolone derivative in a concentration effective to inhibit the fertilization of ova. In addition to effectively inhibiting the enzymes or other sperm components necessary for conception, the compounds used in the method of the invention are advantageous in having low toxic, caustic or irritating properties, so that the contraceptive compositions are suitable for long-term use without adverse side-effects.

6 Claims, No Drawings

CONTRACEPTIVE METHOD

The U.S. government has rights in this invention pursuant to Contract No. AID/DSPE-C40035 awarded by the Agency for International Development.

This invention relates to contraceptive methods and compositions for use in mammals and more particularly to such methods wherein certain pyrazolone derivatives are used as vaginal contraceptive agents.

BACKGROUND OF THE INVENTION

The known compositions which have found practical use as vaginal contraceptives typically incorporate an active ingredient which is spermicidal. In spite of their high spermicidal activity, however, vaginal contraceptives incorporating these materials are not as effective in preventing conception as would be desirable. In addition, there are some indications that these materials possess undesirable side-effects.

In accordance with the invention, there is provided a method for inhibiting conception in mammals in which the contraceptive effects are achieved, not by immobilizing spermatozoa, as in the case of spermicidal contraceptives heretofore known, but by inhibiting sperm transport and/or by preventing certain sperm events necessary for fertilization. It has been found that certain compounds, hereinafter described, function as inhibitors of enzymes or other sperm components necessary for fertilization and have high contraceptive potency when used vaginally in mammals, in a concentration sufficient to prevent fertilization of ova by spermatozoa in the presence of the comounds.

BRIEF DESCRIPTION OF THE INVENTION

In accordance with the method of the invention, there is maintained in the genital tract of a female mammal a pyrazolone derivative in a concentration effective to inhibit the fertilization of ova. The active agent is suitably supplied in the form of a composition including the active agent and a pharmaceutically acceptable base or carrier for facilitating handling, application, and retention. In addition to effectively preventing fertilization, the compounds used in the method of the invention, are advantageous in possessing low toxic, caustic or irritating properties, so that the contraceptive compositions are suitable for long-term use without adverse side-effects.

DETAILED DESCRIPTION

The pyrazolone derivaties used as contraceptive agents in accordance with the invention have the formula

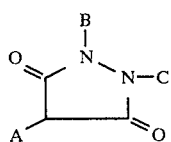

wherein

A is hydrogen, halo, trihalomethyl, lower ($C_1$-$C_8$) alkyl, —X—OH,

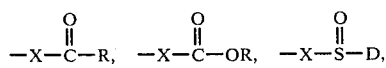

$$-X-S-D, \quad \text{or} \quad -\overset{R_1}{\underset{|}{N}}-R_2,$$

X is a lower ($C_1$-$C_8$) alkylene group,

R, $R_1$, and $R_2$ are hydrogen, or the same or different lower alkyl groups, and B, C, and D, which can be the same or different, are phenyl, hydroxyphenyl or lower alkylphenyl, further provided that B and C together can form the chain

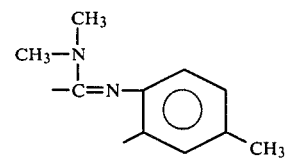

Examples of compounds coming within the scope of the invention include:

4-butyl-1,2-diphenyl-3,5-pyrazolidinedione (phenylbutazone)

4-butyl-1-(p-hydroxyphenyl)-2-phenyl-3,5-pyrazolidinedione (oxyphenbutazone)

4-(3-hydroxybutyl)-1,2-diphenyl-3,5-pyrazolidinedione (hydroxyphenylbutazone)

4-butyl-1-(p-hydroxyphenyl)-2-phenyl-3,5-pyrazolidinedione (γ-hydroxyphenylbutazone)

4-(3-hydroxy)-1-(p-hydroxyphenyl)-2-phenyl-3,5-pyrazolidinedione (p, γ-dihydroxyphenylbutazone)

4-[2-(phenylsulfinyl)ethyl]-1,2-diphenyl-3,5-pyrazolidinedione (sulfinpyrazone)

4-[2-(phenylthio)ethyl]-1,2-diphenyl-3,5-pyrazolidinedione (thio analogue of sulfinpyrazone)

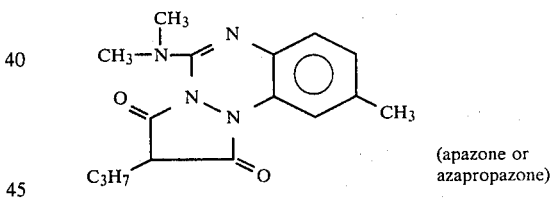

(apazone or azapropazone)

All of the compounds listed above, and methods for their preparation, are known. Analogous methods for the preparation of other compounds within the scope of the invention will be apparent to those skilled in the art. These compounds belong to a group known as pyrazolone derivatives known to be useful as anti-inflammatory agents for treatment of arthritis and related disorders. The contraceptive properties of these compounds, however, has not previously been known.

The invention is illustrated by the following examples.

EXAMPLE 1

4-Butyl-1,2-diphenyl-3,5-pyrazolidinedione

This compound, also known as phenylbutazone, was evaluated for its contraceptive activity in several ways. In one series of tests, the ability of the compound to inhibit the fertilization of hamster oocytes by human spermatozoa (Rogers et al., *Fertil. Steril.*, 32:664, 1979; Binor et al., *Fertil. Steril.*, 33:321, 1980) was evaluated. In another series of tests, mouse spermatozoa were treated with the compound and the ability of the treated spermatozoa to fertilize mouse oocytes in vitro was determined (Reddy et al., *J. Reprod. Fertil.*, 57:437, 1979). In a third series of tests, the compounds were mixed with an appropriate carrier or base and placed in the vaginas of mature female rabbits prior to mating with males of known fertility. After a period of at least 36 hours, the conception rate was determined by sacrificing the animals and determining the number of embryos or fetuses. The compound showed very high contraceptive ability in all of these tests. The compound also prevents the acrosome reaction of spermatozoa, a morphological requirement before the spermatozoa can fertilize eggs.

EXAMPLE 2

4-Butyl-1-(p-hydroxyphenyl)-2-phenyl-3,5-pyrazolidinedione monohydrate

This compound (oxyphenbutazone) was tested for its contraceptive activity by the three series of tests described under EXAMPLE 1 and was found to be equally or more potent as a contraceptive. It also prevents the acrosome reaction of spermatozoa.

For practical use as vaginal contraceptive compositions in accordance with the invention, the active agents are dissolved or suspended in a suitable solvent such as dimethylsulfoxide and mixed with a pharmaceutically acceptable carrier or base to facilitate application to and retention in the genital tract. For this purpose, it is preferred to use a carrier which is viscous or semi-solid, such as a jelly, cream or foam. Examples of suitable carrier materials, which can be used alone or in admixture with appropriate solvents such as water to produce carriers having the desired properties, include polyethylene glycol, sodium carboxymethyl cellulose, acacia and tragacanth. Polyethylene glycol having a molecular weight of about 1,000 is a preferred carrier material.

The concentration of contraceptive agent in the compositions of the invention is suitably about 0.001 to 20 percent by weight and preferably 0.01 to 5 percent. The actual amount of the composition which should be used for optimum results depends on the size and species of the mammal, and can be readily determined by those skilled in the art. It has been found that after the composition has been deposited and spread in the genital tract, a concentration of about 0.01 to 0.5 percent by weight of active agent in solution or suspension provides effective contraceptive properties.

The foregoing detailed description has been given for clearness of understanding only and, no unnecessary limitations should be understood therefrom as modifications will be obvious to those skilled in the art.

What is claimed:

1. A method for inhibiting conception in a female mammal which comprises maintaining in the genital tract of said mammal an effective amount of a compound having the formula

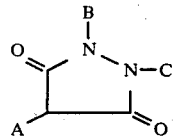

wherein
A is hydrogen, halo, trihalomethyl, lower alkyl, —X—OH,

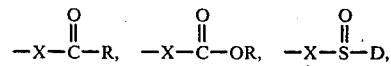

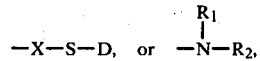

X is a lower alkylene group,
R, $R_1$, and $R_2$ are hydrogen, or the same or different lower alkyl groups, and
B, C, and D, which can be the same or different, are phenyl, hydroxyphenyl or lower alkylphenyl, further provided that B and C together can form the chain

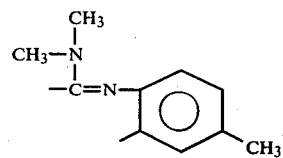

2. The method of claim 1 wherein A is a lower alkyl group, and B and C are selected individually from phenyl or hydroxyphenyl.

3. The method of claim 1 wherein said compound is selected from the group consisting of:
4-butyl-1,2-diphenyl-3,5-pyrazolidinedione
4-butyl-1-(p-hydroxyphenyl)-2-phenyl-3,5-pyrazolidinedione
4-(3-hydroxybutyl)-1,2-diphenyl-3,5-pyrazolidinedione
4-butyl-1-(p-hydroxyphenyl)-2-phenyl-3,5-pyrazolidinedione
4-(3-hydroxy)-1-(p-hydroxyphenyl)-2-phenyl-3,5-pyrazolidinedione
4-[2-(phenylsulfinyl)ethyl]-1,2-diphenyl-3,5-pyrazolidinedione
4-[2-(phenylthio)ethyl]-1,2-diphenyl-3,5-pyrazolidinedione.

4. The method of claim 1 wherein said compound is 4-butyl-1,2-diphenyl-3,5-pyrazolidinedione.

5. The method of claim 1 wherein said compound is 4-butyl-1-(p-hydroxyphenyl)-2-phenyl-3,5-pyrazolidinedione.

6. The method of claim 1 wherein said compound is present in solution or suspension in a pharmaceutically acceptable carrier, in a concentration of about 0.001 to 20 percent by weight.

* * * * *